United States Patent
Hwang

(10) Patent No.: US 12,161,866 B2
(45) Date of Patent: Dec. 10, 2024

(54) SKIN CARE DEVICE PROVIDING MICRO CURRENT TO A MASK FOR PROMOTING PRODUCTION OF COLLAGEN AND ELASTIN

(71) Applicant: N&B LAB CO., LTD., Seoul (KR)

(72) Inventor: Kwang Suk Hwang, Seoul (KR)

(73) Assignee: N&B LAB CO., LTD. (KR)

(*) Notice: Subject to any disclaimer, the term of this patent is extended or adjusted under 35 U.S.C. 154(b) by 706 days.

(21) Appl. No.: 17/341,447

(22) Filed: Jun. 8, 2021

(65) Prior Publication Data
US 2022/0370799 A1    Nov. 24, 2022

(30) Foreign Application Priority Data
May 20, 2021    (KR) .................. 10-2021-0064633

(51) Int. Cl.
| | |
|---|---|
| A61N 1/36 | (2006.01) |
| A61N 1/32 | (2006.01) |
| A45D 44/00 | (2006.01) |
| H01R 12/71 | (2011.01) |
| H01R 13/24 | (2006.01) |

(52) U.S. Cl.
CPC ......... *A61N 1/36014* (2013.01); *A61N 1/325* (2013.01); *A61N 1/327* (2013.01); *A45D 44/002* (2013.01); *A61N 1/328* (2013.01); *H01R 12/714* (2013.01); *H01R 13/2421* (2013.01); *H05K 2201/09036* (2013.01); *H05K 2201/0939* (2013.01)

(58) Field of Classification Search
CPC .... A61N 1/36014; A61N 1/325; A61N 1/327; A61N 1/328; A45D 44/002; H01R 12/714; H01R 13/2421
See application file for complete search history.

(56) References Cited

U.S. PATENT DOCUMENTS

| | | | | |
|---|---|---|---|---|
| 2016/0367189 A1* | 12/2016 | Aimone | ............... | A61B 5/6831 |
| 2018/0292674 A1* | 10/2018 | Bond | ................ | A61F 9/029 |
| 2018/0352937 A1* | 12/2018 | Vandier | ............... | A61B 5/6803 |
| 2019/0217088 A1* | 7/2019 | Claude | ............... | A61N 1/36021 |
| 2022/0257971 A1* | 8/2022 | Kim | ................... | A45D 44/22 |
| 2023/0000683 A1* | 1/2023 | Kang | ................ | A61N 1/04 |
| 2023/0355959 A1* | 11/2023 | Kim | ................... | A61N 1/0492 |

FOREIGN PATENT DOCUMENTS

KR    101691617 B1 * 12/2016

* cited by examiner

*Primary Examiner* — Catherine M Voorhees
(74) *Attorney, Agent, or Firm* — Park & Associates IP Law Office

(57) ABSTRACT

A skin care device formed to cover the left side and right side of a human head and applying a micro current to a mask, includes: a wearing portion extending from the left side of the head through the back side to the right side; and an applying portion formed at each of two ends of the wearing portion and applying the micro current to the mask, wherein the applying portion includes: a conductive portion in contact with the mask; a cover portion to which the conductive portion is coupled and which includes a printed circuit board (PCB) generating the current; and a connecting portion electrically connecting the PCB and the conductive portion to each other, the connecting portion being formed of a conductive spring in elastic contact with the conductive portion.

5 Claims, 7 Drawing Sheets

SKIN CARE DEVICE PROVIDING MICRO CURRENT TO A MASK FOR PROMOTING PRODUCTION OF COLLAGEN AND ELASTIN

FIELD OF THE INVENTION

This application claims the priority benefit of Korean Patent Application No. 10-2021-0064633 filed on May 20, 2021, the entire contents of which are incorporated herein by reference.

BACKGROUND OF THE INVENTION

The present disclosure relates to a skin care device, and more particularly, to a skin care device providing a micro current to a mask for a cosmetic effect to be obtained by allowing the micro current to flow through the mask attached to the user's face for beauty.

A mask pack attached to a user's face to provide a nutrient or moisture to the skin and to clean a pore is widely used due to its ease of use.

The mask pack is manufactured by allowing various cosmetic ingredients to be absorbed into a non-woven fabric or a hydrogel, and may thus have various effects based on the cosmetic ingredients.

In addition to such a mask pack, the user may rub cosmetics applied on the skin with the hand or another tool in order for the cosmetics to penetrate into the skin usually when using the cosmetics to provide the nutrient to the skin or remove a waste product therefrom.

Various devices have been introduced based on ingredients of the cosmetics or for the cosmetics to penetrate into the skin with high efficiency, in which stimulations such as vibration, heat, and micro currents may be applied to the skin mainly using electricity.

When using such a device, the user is required to continuously hold the apparatus in the hand and massage the skin, after applying the cosmetics to the face, etc. Here, the user needs to wash off the cosmetics on the hands and the like, and may thus feel quite uncomfortable. Therefore, the device has been mainly used in a specialized beauty center rather than at home.

Therefore, a new skin care device can be considered for easier use and higher cosmetic effect.

Related Art Document (Patent Document 1) Korean Patent Publication No. 10-2036475, Oct. 25, 2019

SUMMARY OF THE INVENTION

An aspect of the present disclosure may provide a skin care device having a more advanced structure and complex functions.

According to an aspect of the present disclosure, a skin care device formed to cover the left side and right side of a human head and applying a micro current to a mask, includes: a wearing portion extending from the left side of the head through the back side to the right side; and an applying portion formed at each of two ends of the wearing portion and applying the micro current to the mask, wherein the applying portion includes: a conductive portion in contact with the mask; a cover portion to which the conductive portion is coupled and which includes a printed circuit board (PCB) generating the current; and a connecting portion electrically connecting the PCB and the conductive portion to each other, the connecting portion being formed of a conductive spring in elastic contact with the conductive portion.

A protruding portion may be formed along an edge of the cover portion, a sealing portion being formed on an outer periphery of the protruding portion, and a groove corresponding to the protruding portion may be formed in the conductive portion.

The skin care device may further include a relief portion formed on a portion where the wearing portion is in contact with the ear.

The applying portion may be pivotably coupled to the wearing portion at a predetermined angle.

A recessed portion recessed inward from one surface of the PCB may be formed, a conductive pattern having a ring shape may be formed on the recessed portion to be in contact with the conductive spring, and a cylindrical projection formed in the conductive pattern to support the conductive spring may protrude from the PCB.

BRIEF DESCRIPTION OF THE DRAWINGS

The above and other aspects, features and advantages of the present disclosure are more clearly understood from the following detailed description taken in conjunction with the accompanying drawings, in which.

DETAILED DESCRIPTION OF THE INVENTION

Figure 1:
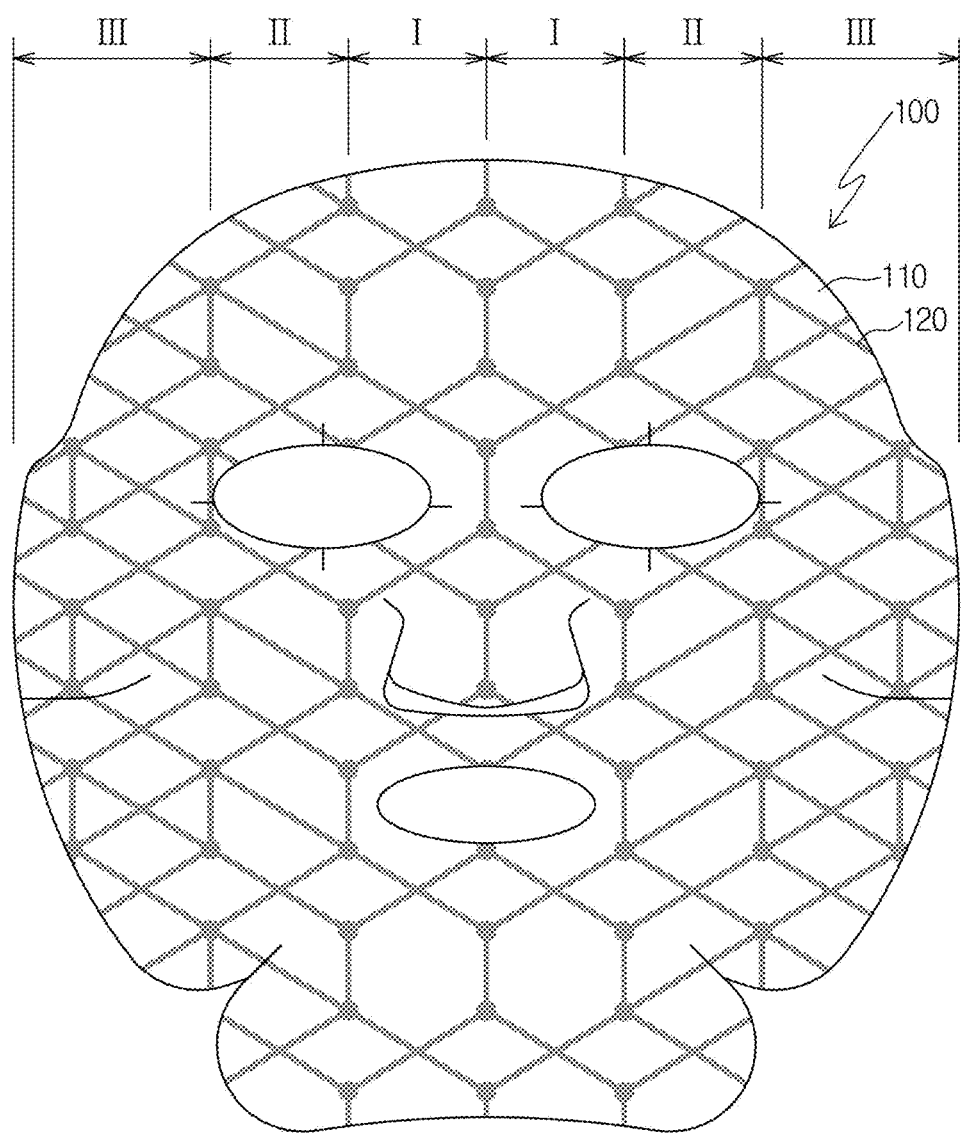
FIG. 1 is a view showing a mask for micro current treatment according to an exemplary embodiment of the present disclosure.

Hereinafter, exemplary embodiments of the present disclosure are now described in detail with reference to the accompanying drawings. An embodiment of the present disclosure explains the present disclosure, and the scope of the present disclosure is not limited to an illustrated embodiment. The illustrated drawings show only essential contents in an enlarged manner to clarify the present disclosure, and omit ancillary ones. Therefore, the present disclosure is not to be construed as being limited to the drawings. In addition, terms "module" and "unit" for components used in the following description are used only to make the disclosure easy to understand. Therefore, these terms do not have meanings or roles that distinguish themselves from each other. Throughout the present disclosure, components that are the same as or similar to each other are denoted by reference numerals that are the same as or similar to each other and a description thereof is replaced by the first description, even in a different exemplary embodiment. In the present specification, singular forms include plural forms unless the context clearly indicates otherwise.

Figure 2:
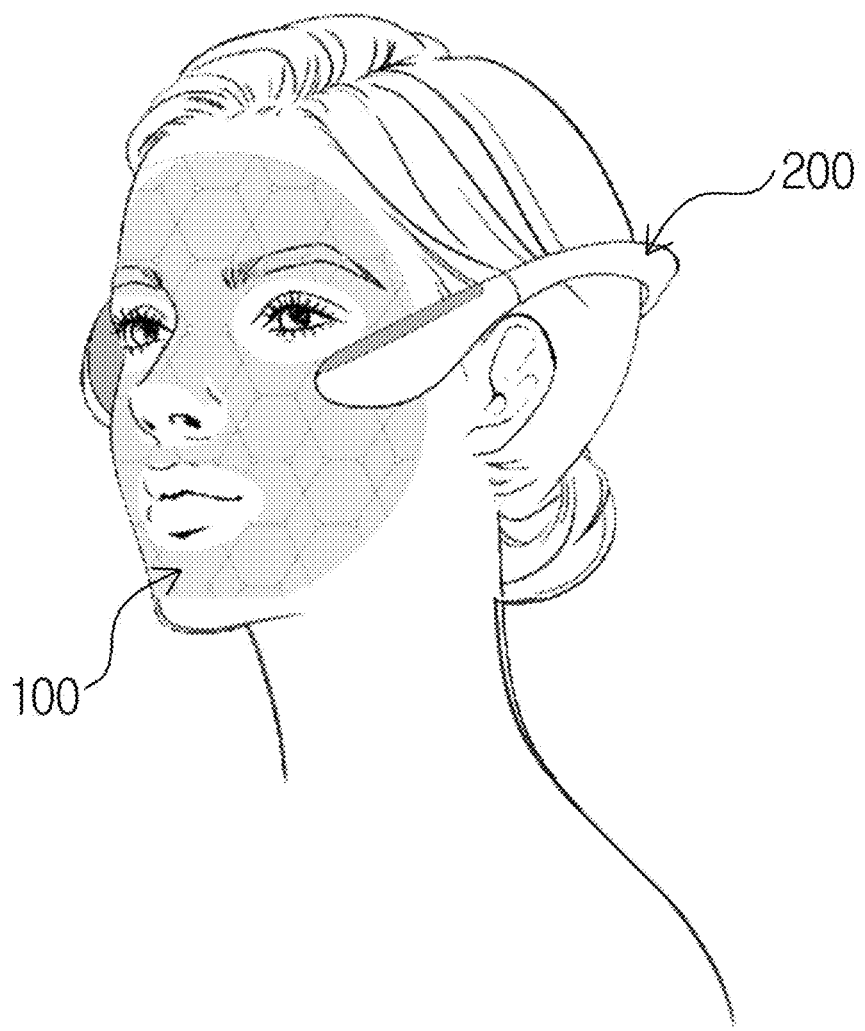
FIG. 2 is a view showing a state in which a skin care device is used according to an exemplary embodiment of the present disclosure.

FIG. 1 is a view showing a mask for a micro current treatment according to an exemplary embodiment of the present disclosure; and FIG. 2 is a view showing a state in which a skin care device is used according to an exemplary embodiment of the present disclosure.

Referring to FIG. 1, the mask for a micro current treatment according to an exemplary embodiment of the present disclosure may include a support 110 and a conductive layer 120 printed on one surface of the support 110. In the present disclosure, the support may be made of a non-woven or woven fiber. The mask may be provided to a final consumer in a state in which a cosmetic substance such as a moisturizer/nutrient is already absorbed into the support, or the cosmetic substance is separately provided and enabled to be absorbed into the support when used by the consumer.

The conductive layer 120 may be formed by printing a conductive material on one surface of the support 110 in a pattern. The conductive material may be a paste or solution containing silver (Ag), aluminum (Al) and nickel (Ni), and may refer to a material in which a printed layer has conductivity during printing.

The conductive material may be printed by various known printing techniques such as inkjet printing, gravure printing, silk screen printing and the like to form the conductive layer.

The pattern may be made of lines connected to each other. As shown in FIG. 1, the pattern may be divided into zones I, II and III, respectively, left and right based on a center line of the mask in the longitudinal direction depending on its shape.

The average areas of the figures arranged in respective zones may be decreased in the order of zone I>zone II>zone III. Such a decrease in the average area may make it possible for more micro current to flow in zone II corresponding to a nasolabial fold area and zone III corresponding to a wrinkle area around the eye. Two or more types of figures may be provided, and the largest figure may have an area in the range of 600 to 1000 $mm^2$ and the smallest figure may have an area of 150 $mm^2$ or less. In addition, it may be effective that a thickness of the line through which electricity flows may be in the range of 1 to 3 mm. The shape of the line may not be limited to a straight line either.

Such an arrangement of figures and repetition of patterns may allow not only the gravure printing or screen printing to be continuously performed on the support (non-woven or woven fabric) provided in the type of a roll, but also stimulation by the micro current to be more efficiently transmitted to the face.

A mask 100 for a micro current treatment of the present disclosure may be manufactured by printing the conductive layer 120 on the support 110 and then cutting positions of the eyes, nose and mouth based on a face shape, and may also be manufactured by forming the face shape as shown in FIG. 1 and then printing the conductive layer 120 thereon.

As described above, the mask 100 for a micro current treatment may be provided to the consumer in a state in which the cosmetic substance is absorbed in a packaging container or in a state in which the cosmetic substance is not absorbed therein.

The mask 100 in a state in which the cosmetic substance is not absorbed may be used by allowing the separately-provided cosmetic substance to be absorbed into the support 110.

As shown in FIG. 2, a user may attach the mask 100 in which the cosmetic substance is absorbed to the face, and then wear a skin care device 200 on the head.

Figure 3:
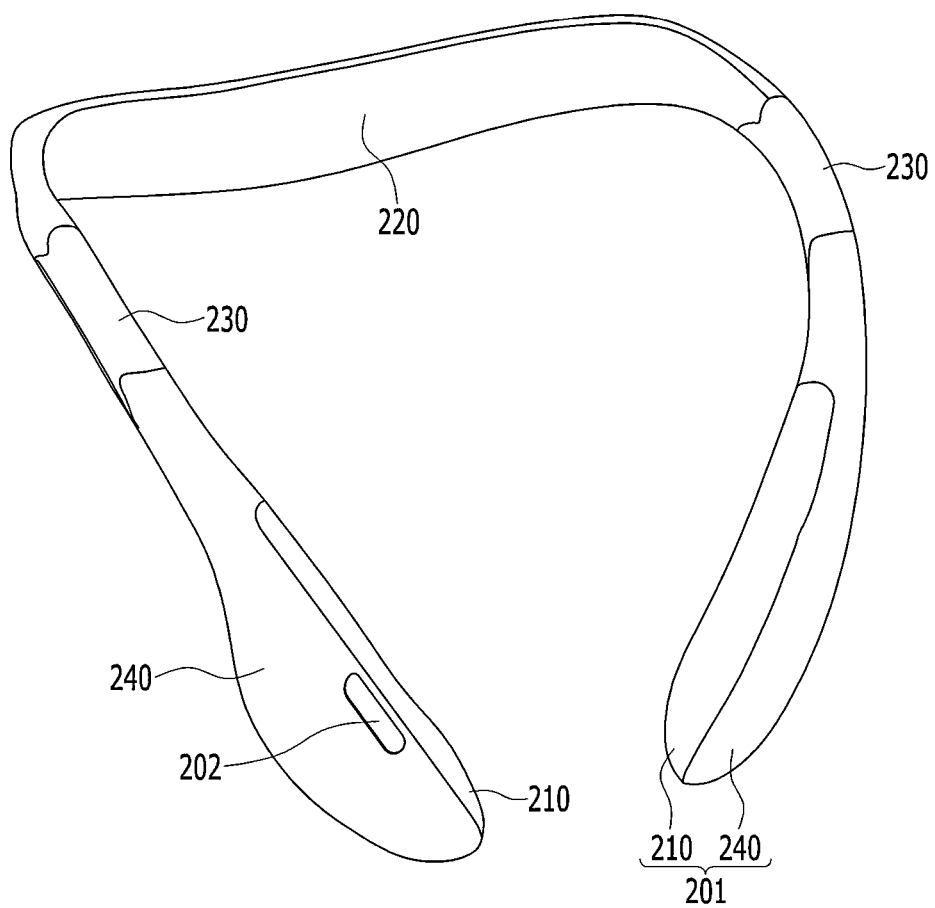
FIG. 3 is a perspective view of the skin care device shown in FIG. 2.
Figure 4:
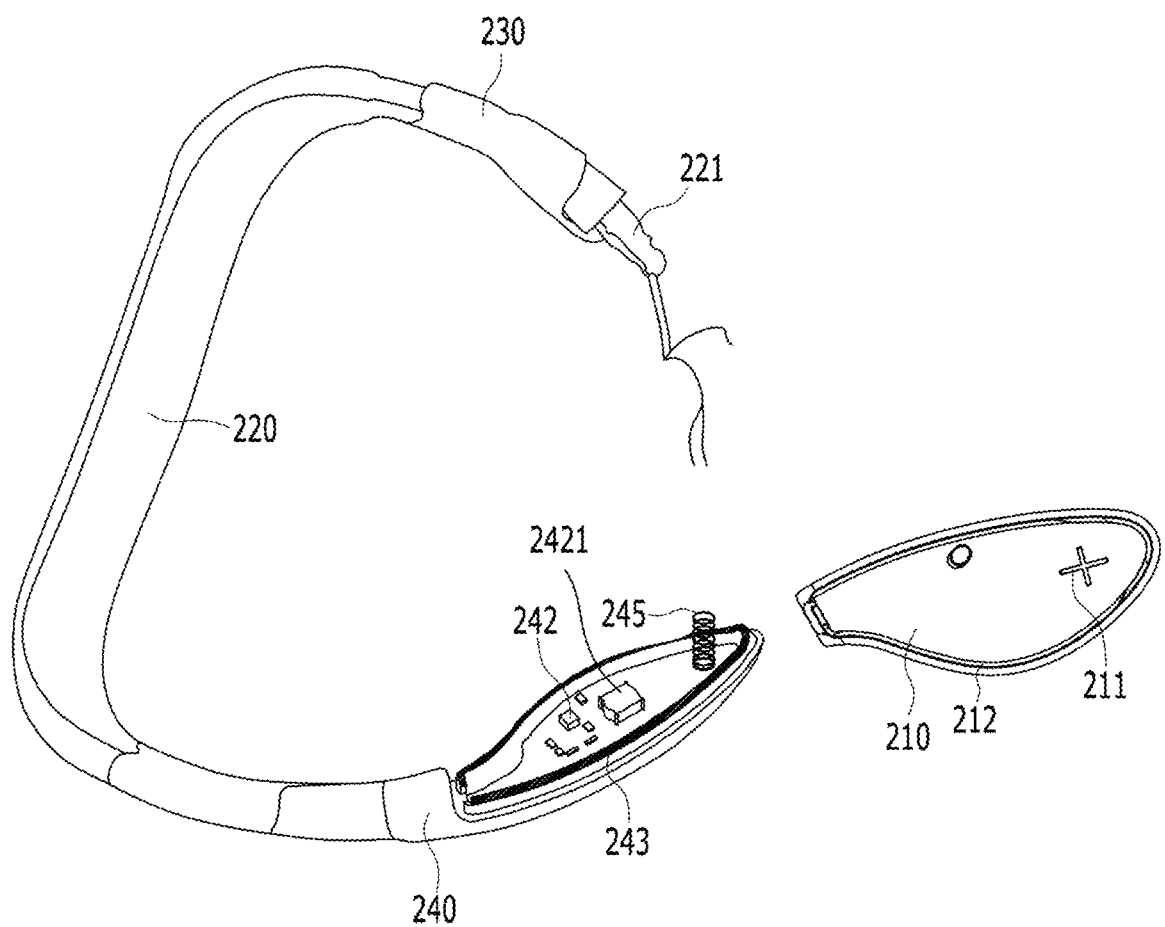
FIG. 4 is a view showing a state in which an applying portion of the skin care device shown in FIG. 3 is exploded.
Figure 5:
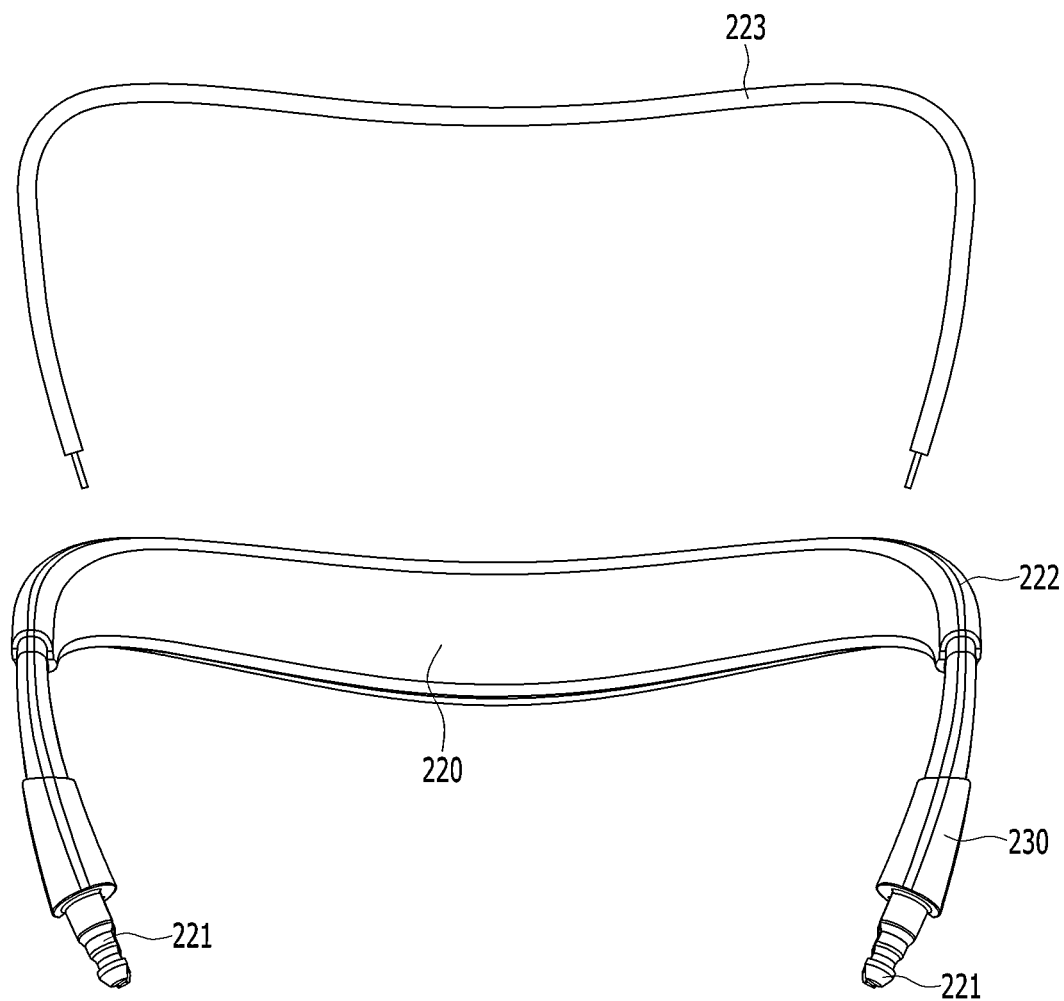
FIG. 5 is a conceptual view showing a wearing portion of the skin care device shown in FIG. 3.
Figure 6:
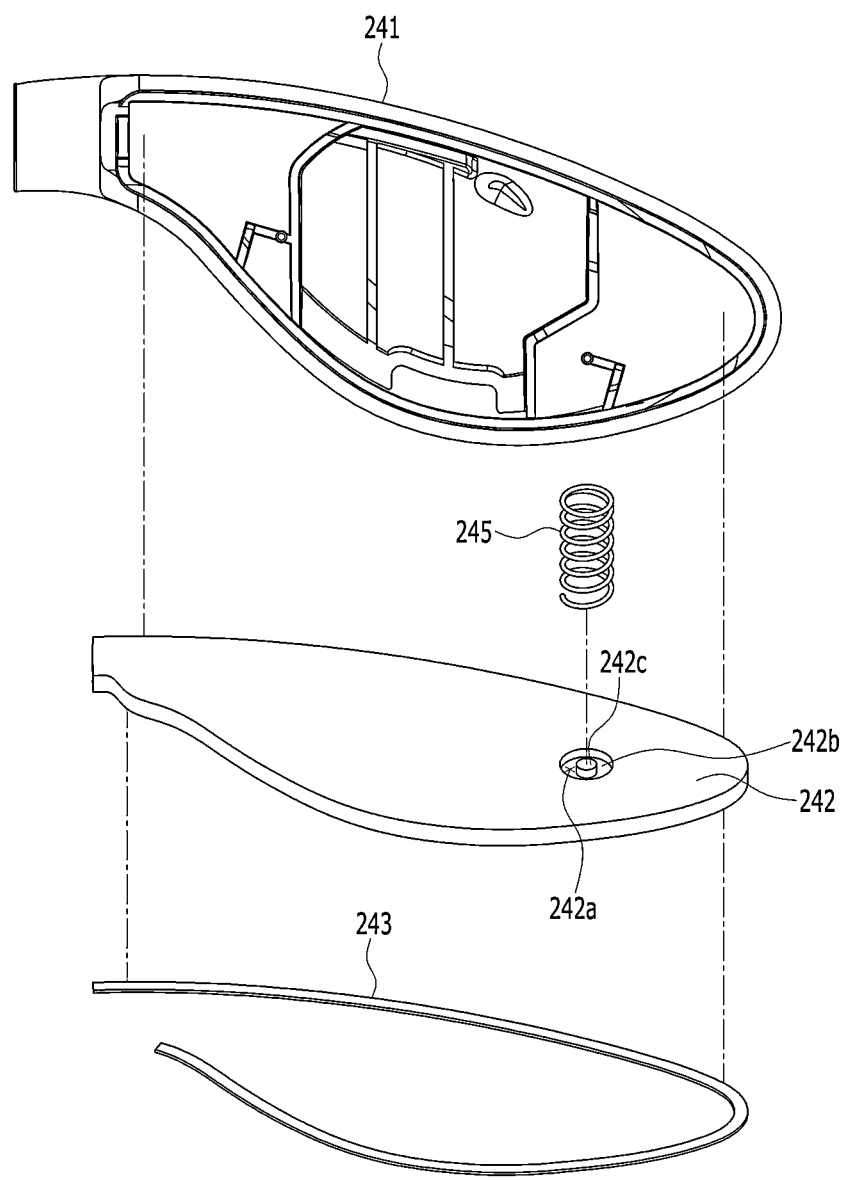
FIG. 6 is a conceptual view showing a cover portion of the skin care device shown in FIG. 3.
Figure 7:
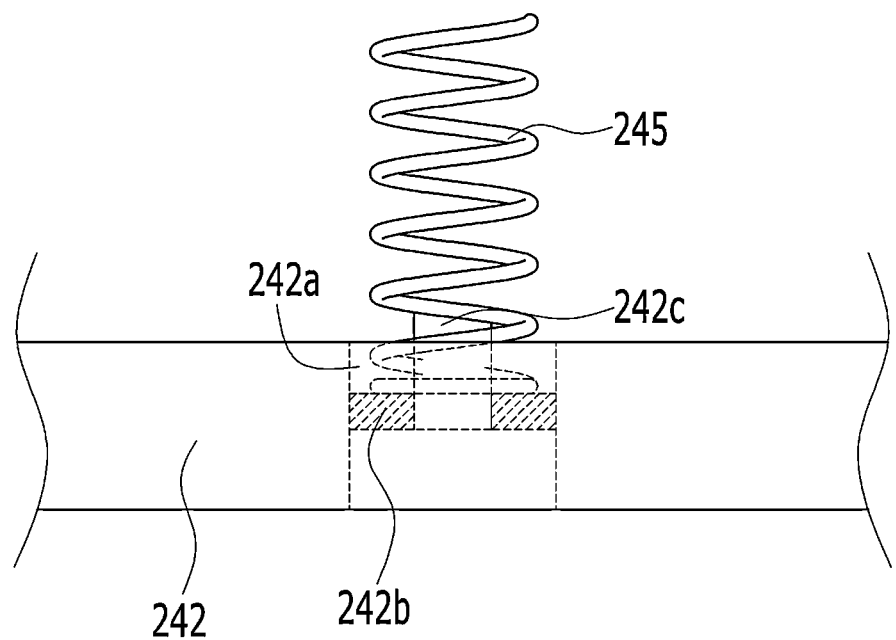
FIG. 7 is a cross-sectional view showing a state in which the printed circuit board (PCB) and spring of the cover portion shown in FIG. 6 are coupled to each other.

FIG. 3 is a perspective view of the skin care device shown in FIG. 2; FIG. 4 is a view showing a state in which an applying portion of the skin care device shown in FIG. 3 is exploded; FIG. 5 is a conceptual view showing a wearing portion of the skin care device shown in FIG. 3; FIG. 6 is a conceptual view showing a cover portion of the skin care device shown in FIG. 3; and FIG. 7 is a cross-sectional view showing a state in which the printed circuit board (PCB) and spring of the cover portion shown in FIG. 6 are coupled to each other.

Referring to FIGS. 3 to 7, the skin care device 200 according to an exemplary embodiment of the present disclosure may include a wearing portion 220 and an applying portion 201.

As shown in FIGS. 2 and 3, the wearing portion 220 may extend from the left side of a human head through the back side to the right side. Referring to FIGS. 4 and 5, the wearing portion 220 may be formed in an overall U-shape, and may include a groove 222 extending from one end to the other end. A wire 223 connecting two ends of the wearing portion 220 to each other may be inserted into the groove 222, and the wire 223 may transmit electricity or a signal generated at one end to the other end. The applying portions 201 coupled to the two ends of the wearing portion 220 through the wire 223 may be electrically connected to each other. For example, a battery may be embedded in either one of the applying portions 201. In addition, a power on-off button 202 and a current generating portion 2421 generating the micro current may be formed on either one of the applying portions 201.

A relief portion 230 may be formed on the wearing portion 220 to cover the wire 223 and the groove 222. The relief portion 230 may be formed on a portion where the wearing portion 220 is in contact with the ear. The relief portion 230 may be formed of a non-conductive material.

Referring to FIGS. 4 to 7, the applying portion 201 in contact with the mask 100 and transmitting the micro current to the mask 100 may be formed at each of the two ends of the wearing portion 220. The applying portion 201 may be pivotably coupled to the wearing portion 220 by a predetermined angle. Accordingly, the applying portion 201 may come into contact with the mask 100 worn on the user's face regardless of the user's face shape; and even if an external shock occurs, it is possible to prevent the wearing portion 220 and the applying portion 201 from being separated from each other and alleviate the shock.

The applying portion 201 may include a conductive portion 210 in contact with the mask 100 and a cover portion 240 to which the conductive portion 210 is coupled. The cover portion 240 may form an exterior of the applying portion 201 and have a space for a printed circuit board (PCB) 242 to be mounted therein. A spherical projection 221 may be formed on each of the two ends of the wearing portion 220 to allow the wearing portion 220 and each of the applying portions 201 to be coupled to each other, and the cover portion 240 may include a ring-shaped coupling portion to surround a portion of the projection 221.

Referring to FIGS. 4 and 6, the cover portion 240 may have the PCB 242 coupled thereto, the PCB 242 generating the micro current in the cover portion 240 and having a controlling portion controlling an overall operation of the skin care device 200. A protruding portion 241 may be formed along an edge of the cover portion 240. In addition, the sealing portion 243 may be formed on an outer periphery of the protruding portion 241. A groove 212 corresponding to the protruding portion 241 may be formed in the conductive portion 210 coupled to the cover portion 240. When the cover portion 240 and the sealing portion 243 are coupled to each other, the sealing portion 243 may come into close contact with the groove formed in the conductive portion 210. The sealing portion 243 may be made of an elastic synthetic resin material. The sealing portion 243 may close a gap between the cover portion 240 and the conductive portion 210 to provide a waterproof function to the skin care device 200, and may prevent a foreign material from being introduced into the applying portion 201 even with vibration or the shock.

Referring to FIGS. 4 and 7, the applying portion 201 may include a connecting portion electrically connecting the PCB 242 and the conductive portion 210 to each other. The connecting portion may be formed of a conductive spring 245 in elastic contact with the conductive portion 210. A recessed portion 242a may be formed in the PCB 242 to be in contact with the conductive spring 245. The recessed portion 242a is a portion recessed inward from one surface of the PCB 242. A conductive pattern 242b may be formed on the recessed portion 242a to be in contact with the conductive spring 245. The conductive pattern 242b may have a ring shape, and a cylindrical projection 242c may be formed in the center of the conductive pattern 242b. The cylindrical projection 242c may be formed to be in contact with an inner periphery of the conductive spring 245. The cylindrical projection 242c may be in contact with and support the conductive spring 245.

When a current is provided to the conductive portion 210, a square wave pulse may be applied to the conductive portion 210, and the minute vibration may thus be generated in the conductive portion 210. Here, the conductive spring 245 may be used to elastically connect the PCB 242 and the conductive portion 210 to each other, through a contact terminal 211 of suitable shape, thereby continuously providing the current to the conductive portion 210 in spite of the vibration or the shock.

The following may also be formed: the battery providing electricity to any one of the applying portions 201; and the controlling portion receiving electricity from the battery and converting the magnitude and form of electricity. The controlling portion can be mounted on the PCB 242. According to a hardware implementation, the controlling portion may be implemented using at least one of an application specific integrated circuit (ASIC), a digital signal processor (DSP), a digital signal processing device (DSPD), a programmable logic devices (PLD), a field programmable gate array (FPGA), a processor, a controller, a micro-controller, a microprocessor or an electric unit performing another function.

The current generating portion 2421 applying the micro current or the square wave pulse to the conductive portion 210 may be mounted on the PCB 242 in the form of a module. The controlling portion and the current generating portion 2421 may be integrally formed with each other or separately formed in the form of the respective modules.

The skin care device 200 may provide the conductive portion 210 with the current of 40 to 100 μA similar to that of a human body. Not only may the cosmetic substance be absorbed into the skin more efficiently, but also production of collagen and elastin under the skin may be promoted, by the stimulation of the micro current delivered to the conductive layer through the conductive portion 210 and then delivered from the conductive layer to the skin through the cosmetic substance and the like, thereby making it possible for the user to have more elastic skin.

The skin care device 200 as described above is not limited to the configuration and method of the exemplary embodiments described above. The exemplary embodiments may be configured by selectively combining all or some of the respective exemplary embodiments with each other for their various modifications to be made.

As set forth above, according to at least one exemplary embodiment of the present disclosure, the skin care device configured as described above may be made of a wearable type which may be worn on the head. In this manner, it is possible to allow the user to have no restriction on his or her action during the treatment and active ingredients in the mask pack to be absorbed into the skin in greater amounts through the micro current and the vibration.

While exemplary embodiments have been shown and described above, it will be apparent to those skilled in the art that modifications and variations could be made without departing from the scope of the present disclosure as defined by the appended claims.

What is claimed is:

1. A skin care device for applying a micro current to the face of a user via a mask, comprising:
a wearing portion extending from the left side of the head of the user through the back side to the right side thereof; and
an applying portion formed at each of two ends of the wearing portion and applying the micro current to the mask,
wherein the applying portion includes:
a conductive portion in contact with the mask;
a cover portion to which the conductive portion is coupled, the cover portion defining a vacant inner space and including a printed circuit board (PCB) mounted within the inner space, and a current generating device mounted on the PCB for generating the micro current; and
a connecting portion for electrically connecting the PCB with the conductive portion, the connecting portion including a conductive spring in elastic contact with the conductive portion for transmitting the micro current from the PCB to the conductive portion and to the mask through the conductive spring,
wherein the PCB includes a recessed portion recessed inwardly from an outer surface of the PCB,
a conductive pattern having a ring shape is formed on the recessed portion to which the conductive spring is placed for transmitting the micro current from the PCB to the conductive portion and to the mask through the conductive spring, and
a cylindrical projection formed on the conductive pattern to support the conductive spring.

2. The skin care device of claim 1, wherein a protruding portion is formed along an edge of the cover portion, a sealing portion formed on an outer periphery of the protruding portion, and
a groove corresponding to the protruding portion is formed in the conductive portion for coupling to the sealing portion upon assembling the conductive portion to the cover portion.

3. The skin care device of claim 1, further comprising a relief portion formed on a portion where the wearing portion is in contact with an ear of the user.

4. The skin care device of claim 1, wherein the applying portion is pivotably coupled to the wearing portion by a predetermined angle.

5. A skin care device for applying a micro current to the face of a user via a mask, comprising:

a wearing portion extending from the left side of the head of the user through the back side to the right side thereof;

an applying portion formed at each of two ends of the wearing portion and applying the micro current to the mask; and a mask formed with a support member configured to hold a cosmetic or healthcare substance therein and a conductive layer printed on one surface of the support member, wherein the conductive layer has a mesh or net pattern formed of line elements connected to one another, the mesh or net pattern covering a major area of the face, wherein the mesh or net pattern defines a relatively smaller mesh size at lateral sides of the mask than at central sides of the mask, wherein the applying portion includes:

a conductive portion in contact with the mask;

a cover portion to which the conductive portion is coupled, the cover portion defining a vacant inner space and including a printed circuit board (PCB) mounted within the inner space, and a current generating device mounted on the PCB for generating the micro current; and a connecting portion for electrically connecting the PCB with the conductive portion, the connecting portion including a conductive spring in elastic contact with the conductive portion for transmitting the micro current from the PCB to the conductive portion and to the mask through the conductive spring.

* * * * *